(12) United States Patent
Gallem et al.

(10) Patent No.: US 9,505,535 B2
(45) Date of Patent: Nov. 29, 2016

(54) DISPOSABLE AMPOULE FOR INSERTION INTO AN AEROSOL GENERATOR

(75) Inventors: Thomas Gallem, Munich (DE); Uwe Hetzer, Munich (DE)

(73) Assignee: PARI Pharma GmbH, Starberg (DE)

( * ) Notice: Subject to any disclaimer, the term of this patent is extended or adjusted under 35 U.S.C. 154(b) by 158 days.

(21) Appl. No.: 14/234,695

(22) PCT Filed: May 16, 2012

(86) PCT No.: PCT/EP2012/059130
§ 371 (c)(1),
(2), (4) Date: Apr. 14, 2014

(87) PCT Pub. No.: WO2013/013852
PCT Pub. Date: Jan. 31, 2013

(65) Prior Publication Data
US 2014/0224815 A1    Aug. 14, 2014

(30) Foreign Application Priority Data

Jul. 26, 2011   (DE) .................. 10 2011 079 810

(51) Int. Cl.
*B65D 81/32* (2006.01)
*A61M 11/00* (2006.01)
(Continued)

(52) U.S. Cl.
CPC .......... *B65D 51/24* (2013.01); *A61M 15/0003* (2014.02); *A61M 15/0028* (2013.01);
(Continued)

(58) Field of Classification Search
CPC ............. A61M 11/00; A61M 11/005; A61M 15/0003; A61M 15/0028; A61M 15/003; A61M 15/0035; A61M 15/0036; B65D 81/32; B65D 81/3205; B65D 81/3277; B65D 51/20; B65D 51/22; B65D 51/24; B65D 51/2807; B65D 51/2814; B65D 51/2828; B65D 51/2835; B65D 51/2878; B65D 1/09; B65D 1/095; A61J 1/06; A61J 1/1406; A61J 1/2006; A61J 1/201; A61J 1/2013; A61J 1/2027; A61J 1/2089; A61J 1/2093

See application file for complete search history.

(56) References Cited

U.S. PATENT DOCUMENTS 3,802,604 A * 4/1974 Morane ................ B65D 51/285
                                                    206/222
4,412,836 A * 11/1983 Brignola ............... A61M 5/286
                                                    604/237
(Continued)

FOREIGN PATENT DOCUMENTS

DE            570 040 C      2/1933
DE         14 86 515 A1      4/1969
(Continued)

OTHER PUBLICATIONS

Translation of the International Preliminary Report on Patentability mailed Feb. 6, 2014 for corresponding international Patent Application No. PCT/EP2012/059130.

*Primary Examiner* — Lynne Anderson
*Assistant Examiner* — Kathryn E Ditmer
(74) *Attorney, Agent, or Firm* — Wolf, Greenfield & Sacks, P.C.

(57) ABSTRACT

An ampoule for insertion into an aerosol generator, in order to atomize a substance (40) contained in the ampoule, comprising: a container portion (10), which forms a chamber (11, 23) for receiving at least one constituent of the substance (40); and an interface portion (20), which is designed for receiving and fixing the ampoule receiving portion of the aerosol generator and has, in a direction in which the ampoule is intended to be inserted into the aerosol generator, a push-up bottom (15, 31), characterized in that the container portion (10) and the interface portion (20) are formed by separate parts and the interface portion is of a closable design.

18 Claims, 8 Drawing Sheets

Figure 1:
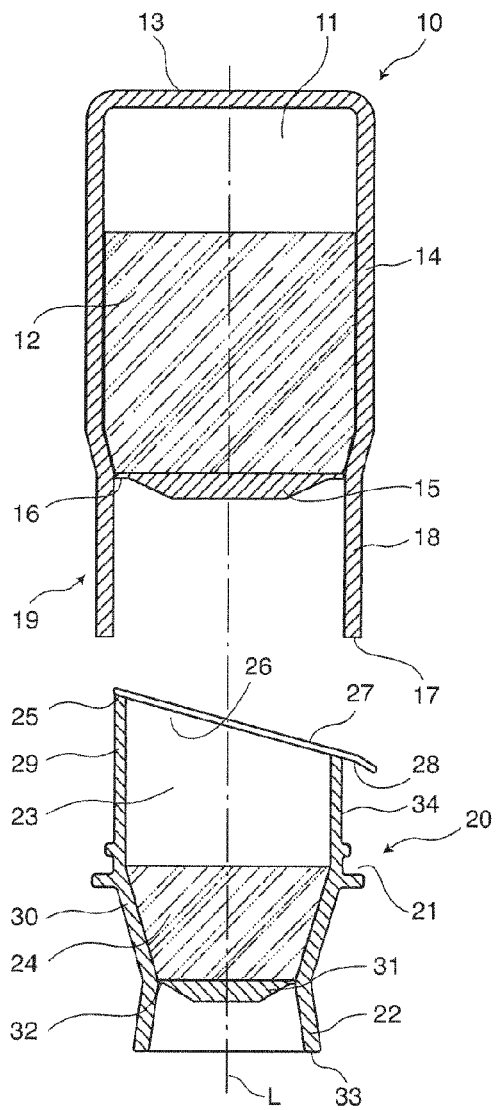
Figure 2:
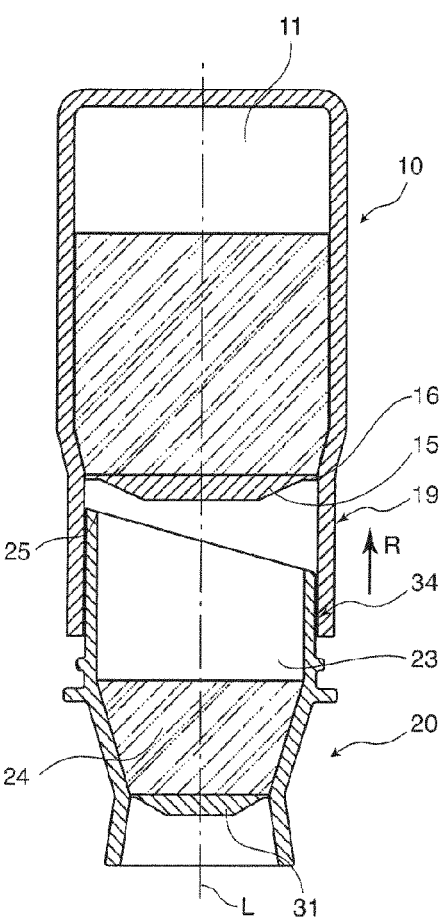
Figure 3A:
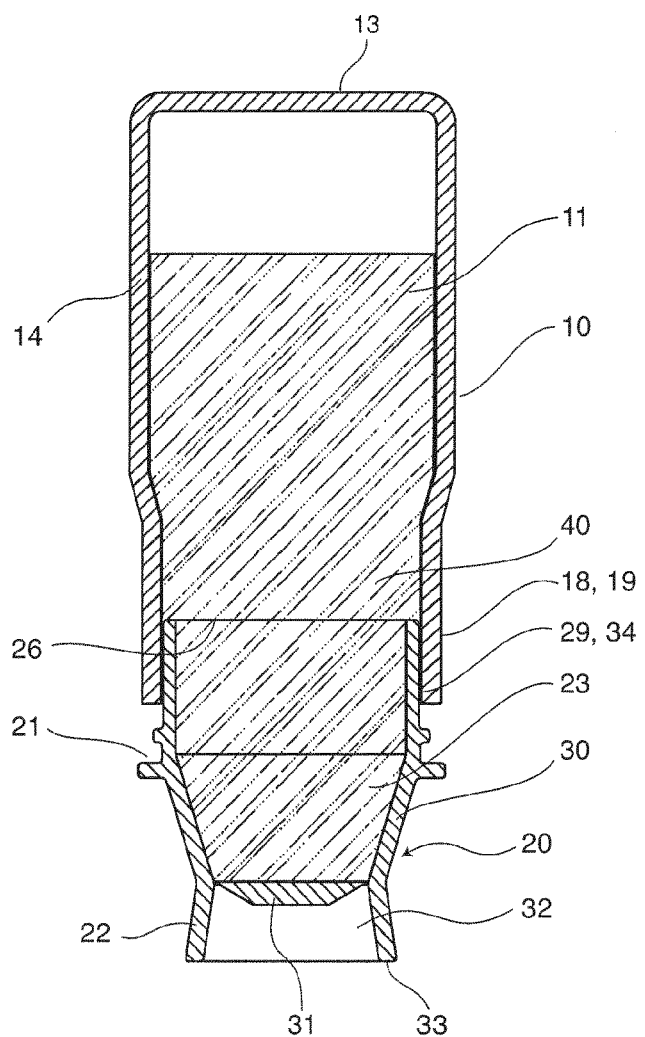
Figure 3B:
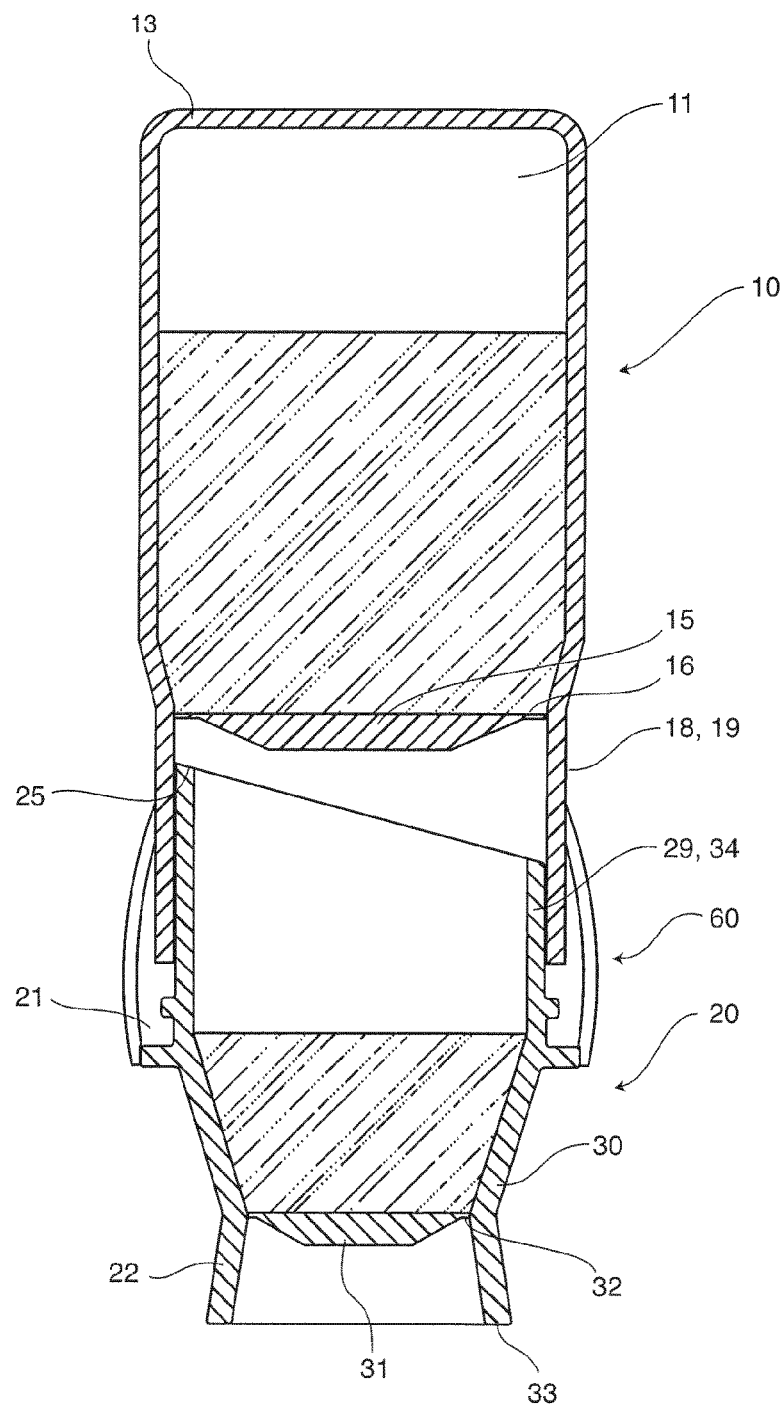
Figure 5A:
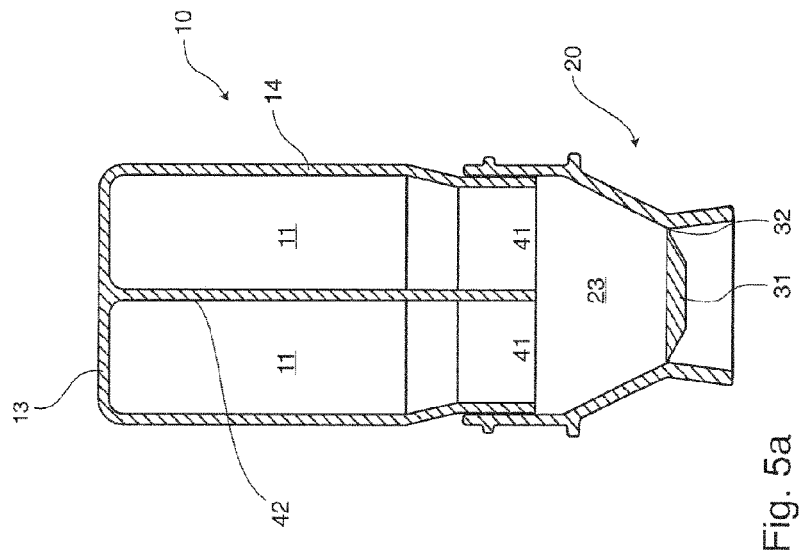
Figure 4:
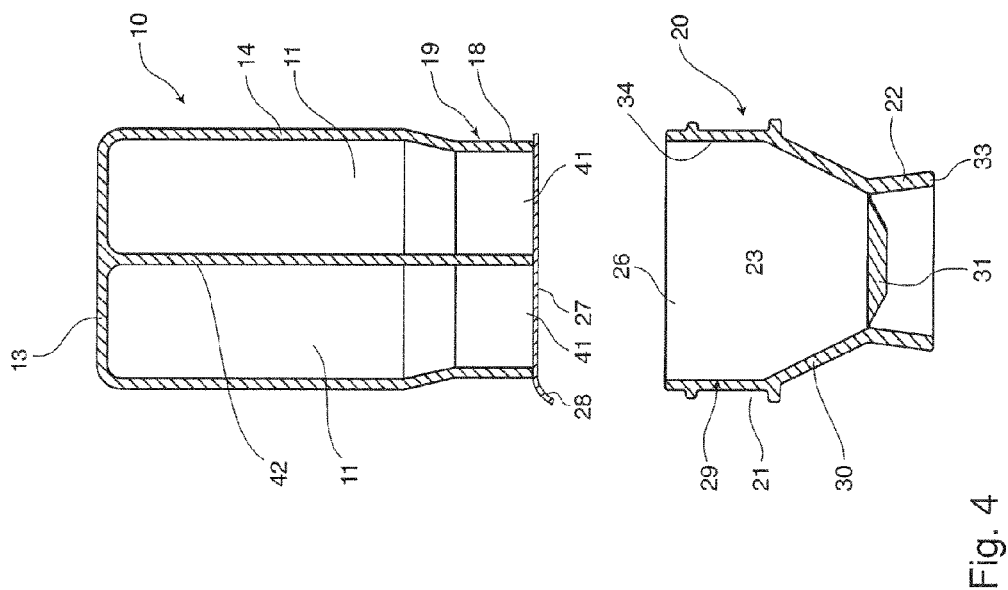
Figure 5B:
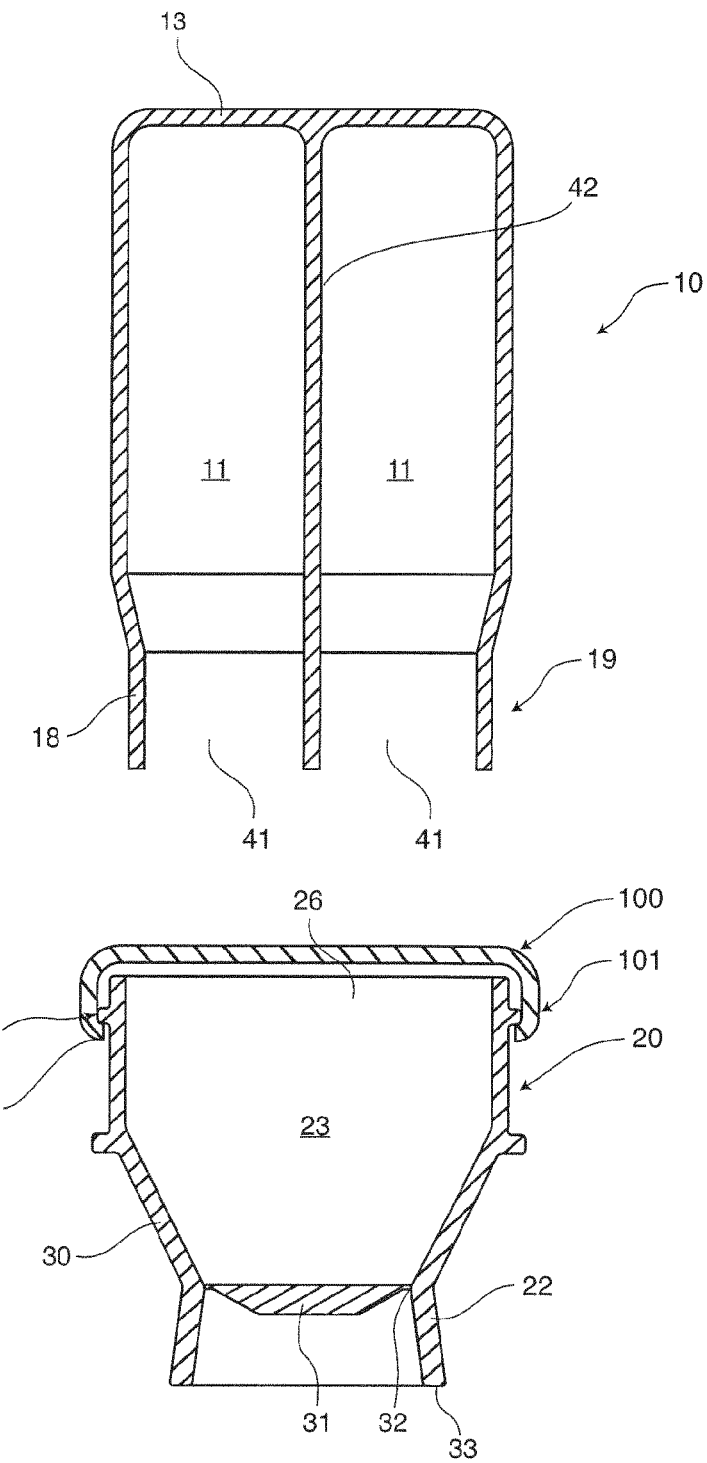
Figure 6:
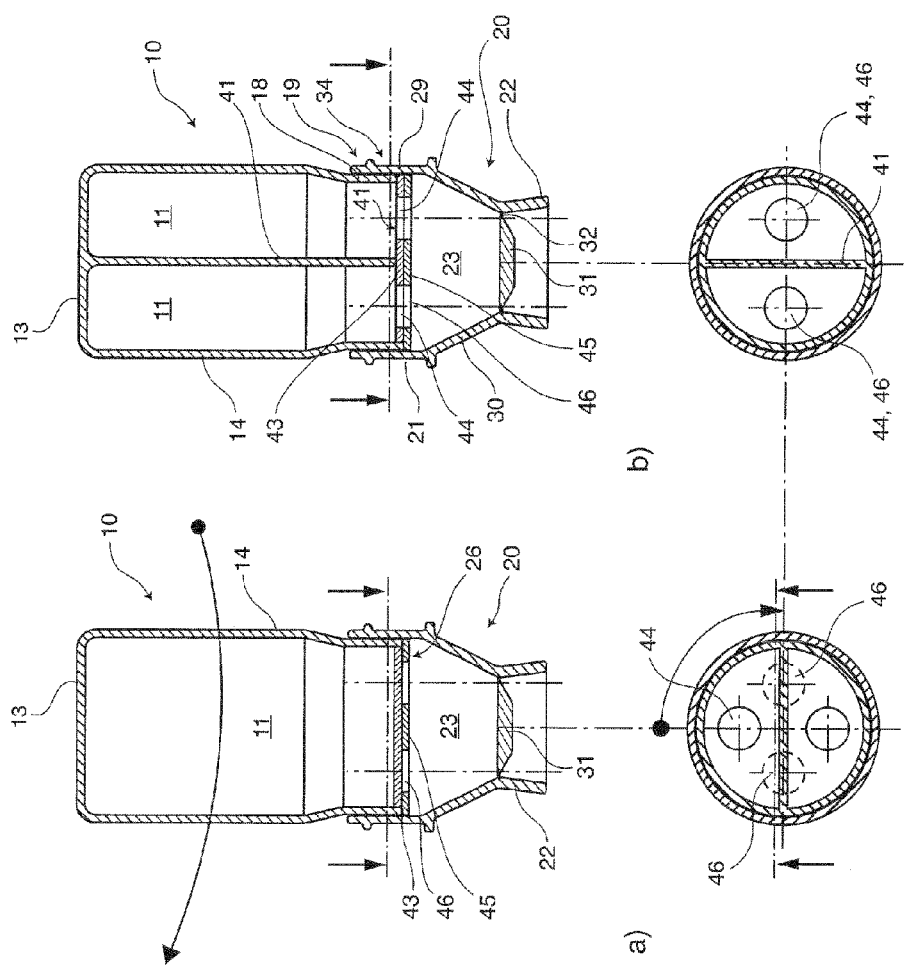
Figure 7:
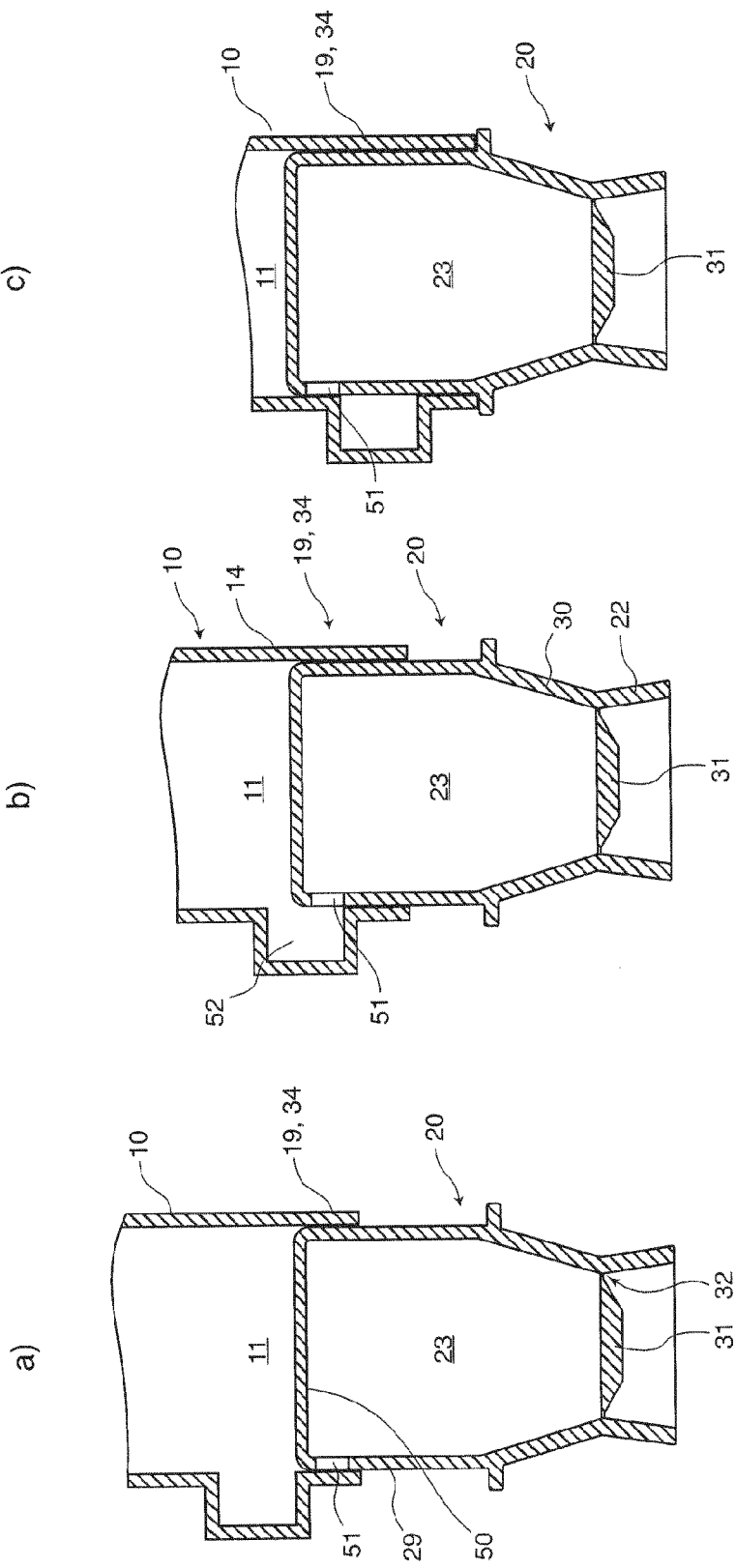

(51) Int. Cl.
*A61M 15/00* (2006.01)
*B65D 51/24* (2006.01)
*B65D 1/09* (2006.01)

(52) U.S. Cl.
CPC ............ *A61M15/0036* (2014.02); *B65D 1/09* (2013.01); *B65D 1/095* (2013.01); *B65D 81/3211* (2013.01); *B65D 81/3277* (2013.01); *A61M 11/005* (2013.01); *A61M 15/0085* (2013.01); *A61M 2207/00* (2013.01); *A61M 2210/0618* (2013.01); *A61M 2210/1039* (2013.01)

(56) References Cited

U.S. PATENT DOCUMENTS

| | | | | |
|---|---|---|---|---|
| 4,858,759 A | * | 8/1989 | Mauthe | B01F 13/002 206/219 |
| 5,167,242 A | * | 12/1992 | Turner | A24F 47/002 128/202.21 |
| 5,474,209 A | * | 12/1995 | Vallet Mas | B65D 51/285 206/219 |
| 6,364,103 B1 | * | 4/2002 | Sergio | A61L 2/18 141/330 |
| 6,997,357 B2 | * | 2/2006 | Fuchs | B05B 11/02 206/222 |
| 7,066,323 B1 | * | 6/2006 | Reisman | B01F 15/0205 206/222 |
| 7,870,952 B2 | * | 1/2011 | Fontana | B65D 51/2814 206/219 |
| 2003/0140921 A1 | * | 7/2003 | Smith | A61J 1/065 128/200.14 |
| 2005/0241634 A1 | * | 11/2005 | Hochrainer | A61J 1/2093 128/200.14 |
| 2009/0137950 A1 | * | 5/2009 | Loenner | A61J 1/067 604/82 |
| 2009/0293868 A1 | | 12/2009 | Hetzer et al. | |

FOREIGN PATENT DOCUMENTS

| | | |
|---|---|---|
| DE | 10 2005 038619 A1 | 2/2007 |
| DE | 10 2007 056462 A1 | 5/2009 |

* cited by examiner

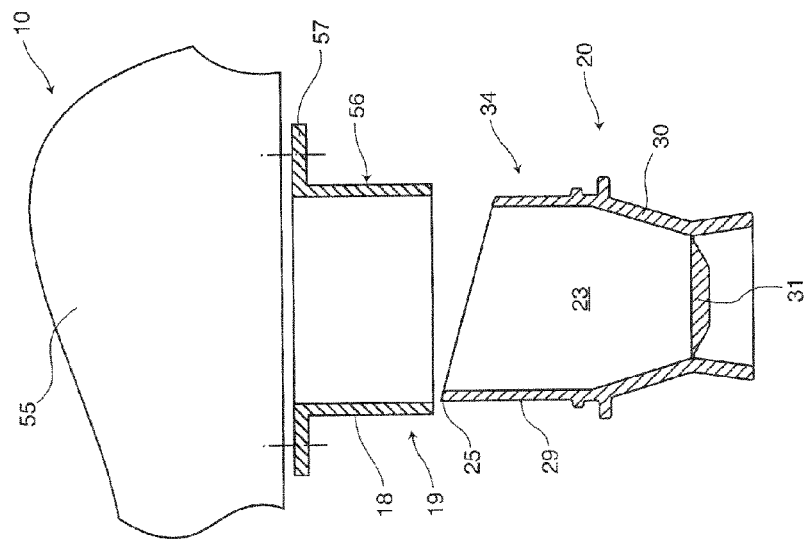
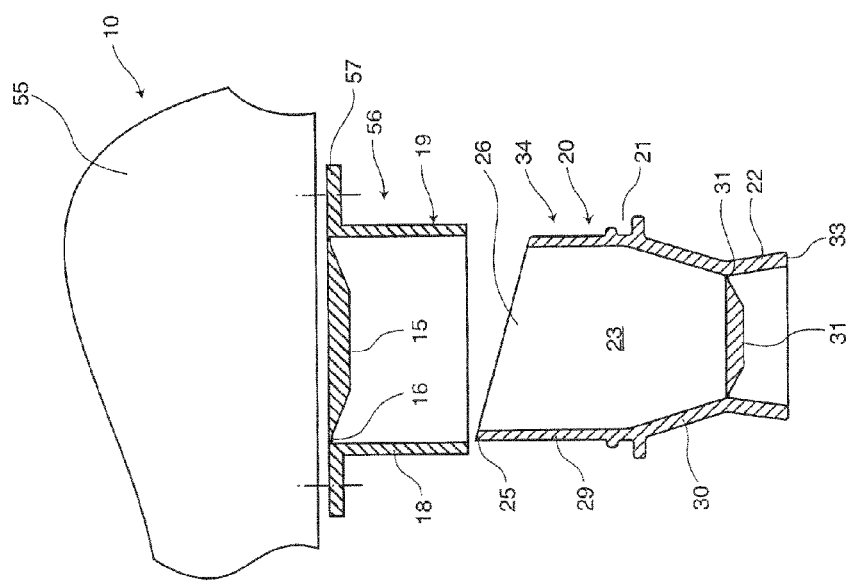

DISPOSABLE AMPOULE FOR INSERTION INTO AN AEROSOL GENERATOR

The present invention relates to ampoules, more particularly to ampoules with interfaces. In particular, the present invention relates to ampoules for use in aerosol generators, i.e. in devices that can be used to generate aerosols for topical application on the skin or in body cavities or openings such as, for example, the nose, lungs, joints and the abdomen, to diagnose, prophylactically prevent, immunize against and/or treat diseases and conditions in humans and animals.

Ampoules of this kind are known from DE 10 2005 038 619 A1 or DE 10 2007 056 462 A1. These ampoules are generally produced in one piece in a so-called blow-fill-seal process while at the same time being filled with the substance to be atomized. These ampoules are mainly used as disposables, so-called disposable ampoules. As regards the design and geometry of these ampoules, account must be taken not only of the requirements for accommodation and fixation in the receiving portion of the aerosol generator, but also of the requirements to be met by this manufacturing process.

However, specifically in the medicinal product sector a large number of other packaging formats have become established in addition to the so-called blow-fill-seal ampoules, which in terms of their design, e.g. the material used, are often adapted to the substance contained therein. Different materials or manufacturing techniques can be used here such as, for example, opaque (coloured) or transparent glass and/or plastics (e.g., brown glass, injection moulded plastics as bottles, blisters, vials, vessels, cartridges, reservoirs, etc.).

The packaging forms should be hygienically safe, which applies both to the material and to the manufacturing process (cleanroom and/or sterile processing conditions). A coating may be provided, as appropriate. Besides hygienic properties, this may influence and/or dictate stabilizing properties or further chemical and physical properties.

The problem of the prior art ampoules described at the outset which are produced in one piece using the blow-fill-seal technique, lies in the fact that the requirements placed on the material of the ampoule as a result of its content or use cannot always be satisfied by the blow-fill-seal technique (the material must be compatible with this technique). The use of other materials thus requires a new manufacturing technique.

In addition, there are substances, e.g. medicines, the constituents of which must be kept separate before administration and are not to be brought together, combined or mixed until just before they are administered. This is impossible, or possible only to a limited extent, with the hitherto known ampoules for use in aerosol generators and with the blow-fill-seal process.

The object of the present invention thus lies in improving an ampoule, more particularly a disposable ampoule of the kind referred to at the outset, to the effect that its design is substantially independent of the manufacturing and filling process and allows its use with a variety of different substances, particularly also substances which are not to be mixed, prepared or dissolved from several constituents until right before being atomized.

The basic idea underlying the present invention is to separate the known ampoule into two or more functional areas or parts. This separation of the ampoule into a container portion and an interface portion (which can also be understood as an adapter) allows the interface portion (adapter) to be produced in a process separate from the filling process, which, on the one hand, permits the use of a variety of different manufacturing and filling procedures and, on the other hand, provides scope for design options, particularly as regards the interface portion. This also makes it possible to implement a dual-chamber system (or multi-chamber system) in which the respective chambers contain different constituents of the substance to be atomized which can be mixed (combined, prepared or dissolved) right before being atomized, and to select materials for the container portion which are adapted to the substance to be atomized. The ampoule for insertion into a receiving portion of an aerosol generator, to atomize a substance contained in the ampoule, accordingly comprises a container portion and an interface portion. The container portion defines a chamber having at least one constituent of the substance received therein. However, the entire substance to be atomized may just as well be already contained in the chamber. In particular, the substance is preferably a liquid substance immediately before being atomized. The interface portion, on the other hand, is preferably designed to receive and fix the disposable ampoule in the receiving portion of the aerosol generator as described in DE 10 2005 038 619 A1 or DE 10 2007 056 462 A1 cited at the outset. In other words, anything to adapt or receive and fix the ampoule in the receiving portion of the aerosol generator is preferably realized solely by appropriate features and elements of the interface portion. By contrast, the container portion is designed only as a packaging case for the substance constituent or the substance to be atomized by the aerosol generator. Therefore, the interface portion is designed to receive and fix the ampoule in the receiving portion of the aerosol generator. It further has a bottom which can be pushed open in a direction in which the ampoule is to be inserted into the aerosol generator. In this regard, a direction in which the ampoule is to be inserted into the aerosol generator is to be understood as meaning the direction in which the ampoule is to be moved relative to the push-open member or mandrel of the aerosol generator in order to push the bottom open. It is, for example, conceivable for the receiving portion of the aerosol generator to be designed stationary and for the ampoule to be pressed against the push-open member or mandrel into the receiving portion, whereby the bottom is pushed open. As an alternative possibility, it is also conceivable, as described in the aforementioned prior art, to fix the ampoule in a lid of the aerosol generator and to insert the ampoule into the aerosol generator by screwing or attaching the lid to the aerosol generator, thereby pushing the bottom open. Both variants are covered by the selected wording. The present invention is characterized in that the container portion and the interface portion are formed by separate parts which each comprise a connecting region in which the container portion and the interface portion are or can be connected to each other. It is conceivable in this respect for the connection to be made by the manufacturer, for which purpose hot work processes (welding techniques), bonding processes, screwing, latching or any other method for interlocking the separate parts can be selected, for example. The region connecting the parts is, in particular, designed so that the same or different methods can be used to connect the interface portion to container portions made of a variety of different materials. Foil blisters, blow-moulded receptacles, injection-moulded receptacles as well as glass jars, and also receptacles produced using the blow-fill-seal technique, are conceivable as container portions. The interface portion preferably is an inexpensive injection moulded plastic part. As an alternative or in addition thereto, it is also conceivable for the interface portion to be closed by a lid after being filled with the substance(s) from the container portion, which can also be done by using the connecting region of the interface portion. The separation of the container from the interface portion makes it possible to select optimal manufacturing and filling methods adapted to suit the requirements on the interface portion and/or the container portion, as a result of which the design freedom is considerably increased and a wide variety of combinations are conceivable. In this respect, it is particularly advantageous for the interface portion to be always designed in the same manner, independently of the container portion, ensuring that always the same interface portion can be used for different container portions.

According to a preferred embodiment, it is conceivable—particularly if the container portion and the interface portion are connected for the first time by a final consumer—for the container portion to be also provided with a push-open bottom in the direction in which the ampoule is to be inserted into the aerosol generator, in which case the interface portion has, on the opposite side to its bottom, a push-open member, e.g. a hollow mandrel, for opening the container bottom.

In this arrangement, it is conceivable, on the one hand, for the push-open member to be designed so that the container bottom is pushed open as the container portion is being connected to the interface portion. In other words, the final consumer, for example, will connect the container portion to the interface portion, for instance by screwing or latching them together, in which case a thread or bayonet lock can be used for the screwing operation. While this connection is being made, the container portion and the interface portion also undergo relative motion towards each other, i.e. along the longitudinal direction of the ampoule in a direction in which the ampoule is to be inserted into the aerosol generator. During this motion, the push-open member, e.g. the hollow mandrel, pushes through the bottom of the container portion, similarly to the push-open member of the aerosol generator pushing through the push-open bottom of the interface portion. As regards detailed configurations of this variant, reference is made to the prior art cited at the outset.

As an alternative, it is also conceivable for the container portion and the interface portion to be non-detachably or inseparably connected to each other (by the manufacturer, the hospital, a doctor, or in the patient's home), preferably in advance or prior to inhalation, with there still being relative displacement in the direction of the longitudinal axis of the ampoule or the insertion direction of the ampoule. In this case, the push-open member is designed such that the bottom of the container portion is pushed open by the relative motion between the container portion and the interface portion after the container portion and the interface portion have been connected. This relative motion can be generated by pressing the two or more portions against each other or by pegs on the interface portion or the container portion which engage in appropriate thread grooves in the container portion or the interface portion, such that rotation of one portion relative to the other results in said relative motion and pushes the bottom of the container portion open. The aforementioned pegs may take the form of mandrels, adapters, moulded parts, and/or fittings.

To implement said dual-chamber (or multi-chamber) system, it is particularly preferred for the interface portion to also form a chamber and to have an opening in the region of the push-open member for connection of the chamber of the container portion to the chamber of the interface portion after the bottom of the container portion has been opened. This can be achieved, for example, by the aforementioned hollow mandrel as the push-open member.

In one embodiment of the invention, the chamber of the interface portion is preferably sealed. To this end, the opening of the interface portion can be closed with a seal. When a dual-chamber (or multi-chamber) system of this kind is used, the chamber of the interface portion contains one constituent of the substance to be atomized, whilst the other constituent is present in the chamber of the container portion. The two or more constituents may contain substances, active ingredients, active components, excipients, carrier solutions, degradation products and the like, which find use in medical, therapeutic, diagnostic, immunization and/or analytic applications. By pushing open the bottom of the container portion and opening the seal, the two constituents can be mixed together and atomized following insertion of the ampoule into the aerosol generator. The constituents may contain identical and different ingredients (e.g. active ingredients in the form of a powder, lyophilizate and/or liquid, such as a carrier solution) in the different chambers, in which case the inhalation solution or suspension to be atomized can be formed, for example, by mixing a carrier solution with the active ingredient in the form of a powder or lyophilizate. It is moreover possible to combine, mix or prepare two or more liquids such as, for example, two or more liquids containing different substances.

The container portion and/or the interface portion are preferably formed integrally (from one piece) and/or connected and/or form a unit at the premises of the user (e.g. manufacturer, doctor, hospital, medical staff, or patient).

In addition, in a preferred embodiment, the container portion and/or the interface portion are preferably designed to have rotational symmetry about a longitudinal axis. This may, for example, facilitate the manufacturing process or allow freedom in insertion by eliminating orientation requirements.

In addition, in another preferred embodiment, the container portion and/or the interface portion are preferably not designed to have rotational symmetry about a longitudinal axis, for example to prevent rotation in the aerosol generator or to deliberately set a specific orientation.

The bottom of the interface portion and/or the bottom of the container portion may lie in a plane perpendicular to the longitudinal direction or the direction in which the ampoule is to be inserted into the aerosol generator. In addition, it is advantageous, as described in DE 10 2007 056 462 A1, for both the interface portion and/or the container portion to have a circumferential collar which extends a wall of the respective portion beyond its bottom in its longitudinal direction, i.e. in the direction in which the ampoule is to be inserted into the aerosol generator, in order to appropriately protect the bottom and any predetermined breaking point that may surround the bottom. In this arrangement, the collar of the container portion can preferably be implemented by the connecting region. At the same time, the collar may fulfil the function of a sealing surface that seals the container portion against the interface portion or the interface portion against the aerosol generator.

Also, it is preferred for the interface portion to have a circumferential, outwardly open groove in a wall to fix the ampoule in the receiving portion of the aerosol generator, e.g. a lid of the aerosol generator. As regards specific configurations of this kind, reference is also made to the prior art cited at the outset.

In addition to the ampoule (ampoules and/or ampoule chambers), the present invention also proposes an interface portion of (or for) such an ampoule, which comprises all of the components necessary for cooperation with the aerosol generator and which has a connecting region for connection with a container portion as described above, to form the ampoule.

Preferably, the connecting region is designed as a thread and/or in the manner of a bayonet lock. Likewise, the connecting region (or the coupling system) can take the form of a locking, latching or screw mechanism, a Luer taper, or the like. Snap-on, lock-on, clamp, coupling-fit, sealing, bonded and/or adhesive connections are also conceivable alternatives.

The separate production of the interface portion offers more scope for the design of such ampoules and ensures high-precision and reproducible manufacturing of all components that are functionally relevant to the connection with the aerosol generator, particularly those in the bottom of the interface portion and the optionally provided collar of the interface portion which may also serve as a seal against the push-open member, e.g. the hollow mandrel of the aerosol generator.

The resulting large number of possible combinations of the interface portion with various kinds of container portions of different materials and different designs makes it possible to select a method for producing and filling the container portion which is tailored to the packaging and filling process.

The ampoule can be of an open or closed design. Also, the interface portion may be empty and filled from the container portion during use. As an alternative or in addition, the interface portion may be closed by a detachable or non-detachable lid after it has been filled from the container portion.

A diaphragm is also conceivable as a closure (seal) of the ampoule or container portion and/or of the interface portion. This diaphragm may allow the ampoule or container portion and/or the interface portion to be refilled, for example by means of a syringe.

The interface portion may also be connected to one or more container portions to form the ampoule. The connection (or coupling) may be releasable or permanent. This joining of the interface portion to form the ampoule may serve to provide a gas- and/or liquid-tight seal for the ampoule.

A permanent connection is used to implement a disposable ampoule, for example to prevent refilling. The connection may be designed as a safe closure (or coupling) in the form of, e.g., a locking, latching or screw mechanism, a thread, Luer taper, bayonet lock, or the like.

The connecting regions of the container and/or interface portions, which may be the same or different, can be made from the same or different materials. Soft and hard plastics can be considered here. Coatings which promote and/or improve the connection properties are also conceivable.

In addition, the separation into two or more functional areas or two or more parts makes it possible to implement a dual- or multi-chamber packaging, as has already been explained above.

Further features and advantages of the present invention, which may be implemented alone or in combination with one or more of the above features unless these are irreconcilable, will be apparent from the following description of preferred embodiments in which reference will be made to the accompanying drawings, in which:

FIG. 1 is a longitudinal section taken through an ampoule according to the present invention in which the container portion and the interface portion are not connected;

FIG. 2 shows the ampoule from FIG. 1 with the container portion connected to the interface portion;

FIGS. 3*a* and 3*b* show an ampoule according to two embodiments with the container portion connected to the interface portion;

FIG. 4 shows an ampoule according to another embodiment in which the container portion and the interface portion are not connected;

FIG. 5 shows the ampoule from FIG. 4, with the container portion connected to the interface portion in FIG. 5*a*, and with the interface portion closed by a lid in FIG. 5*b;*

FIG. 6 shows an ampoule according to another embodiment, comprising a container portion with two chambers, with a) showing a condition in which the container portions are not in fluid communication with the interface portion, and b) showing a condition in which the chambers of the container portion are in fluid communication with the interface portion;

FIG. 7 shows, in FIGS. 7*a* to *c*, a sequence of motions of another embodiment of an ampoule according to the invention, in which the interface portion is pushed step by step into the chamber of the container portion; and FIGS. 8*a* and *b* show further embodiments of an ampoule according to the invention in which part of the container portion is formed by a bag.

It will be appreciated that identical or comparable elements in the accompanying drawings are identified by the same reference numerals and that these identical or comparable elements will not be described again in the various embodiments for the sake of avoiding repetition.

The disposable ampoule depicted in FIGS. 1 and 2 is a dual-chamber ampoule. It comprises a container portion 10 and an interface portion 20.

In the depicted embodiments, the container portion 10 has a cylindrical basic shape which substantially has rotational symmetry about its longitudinal axis L. The container portion 10 forms a chamber 11 (first chamber) containing a first constituent 12 of a substance to be atomized in an aerosol generator (not shown). The chamber 11 is closed on an opposite end of the container portion 10 to the interface portion 20 by a front wall 13 extending substantially perpendicularly to the longitudinal axis L, by the wall 14 formed by the cylinder jacket, as well as by a bottom 15 which also extends perpendicularly to the longitudinal axis L and which is surrounded at least along part of its circumference by a predetermined breaking point 16. The bottom 15 is situated at a distance from the front wall 17 of the container portion 10 opposite the end wall (cover surface) 13. To this end, the wall 14 is extended starting out from the end wall 13 in the direction of the longitudinal axis L beyond the container bottom 15, forming a collar 18. The collar is designed as a connecting portion 19 for connection with the interface portion 20.

The interface portion 20 comprises the structural elements for connection with or accommodation and fixation in the aerosol generator (not shown). It comprises a circumferential groove 21 as well as a collar 22, as are required in DE 10 2007 056 462 A1 as structural elements for accommodation and fixation in the aerosol generator described therein. Furthermore, the interface portion 20 defines another chamber 23 (second chamber) containing a second constituent of the substance to be atomized, e.g. a powder-form active ingredient of a medicine. On its end facing the container portion 10 in the longitudinal direction L there is formed a push-open member 25 in the form of a hollow mandrel that describes an opening 26 which is in fluid communication with the chamber 23 or communicates there-with. In the embodiment shown, this opening is tightly closed by a seal 27. The seal 27 comprises a grip tab 28 for removing the seal 27 from the opening 26 and exposing the chamber 23. The chamber 23 is limited by the seal 27, a cylinder wall 29 in the upper region of the interface portion 20, as well as by a frustoconically tapering channel 30 which continues from the cylinder wall 29 on the end facing away from the container portion 10. Another boundary is constituted by the bottom 31 comprising the predetermined breaking point 32 which extends at least in part along the circumference. The bottom 31 is likewise disposed perpendicularly to the longitudinal axis. The collar 22 extends from the end of the frustoconical portion 30 which faces away from the cylinder wall 29 and in the direction of the longitudinal axis, away from the cylinder wall 29 and beyond the bottom 31 in the longitudinal direction L, to form the collar 22, such that the bottom is situated at a distance from the front wall 33 in a protected position as described in DE 10 2007 056 462 A1. The cylinder wall 29 forms at the same time the connecting region 34 for connection with the connecting region 10 of the container portion 10.

In one embodiment, it is conceivable for the container portion 10 and the interface portion 20 to be supplied together as separate units that must first be connected by the final consumer for use in an aerosol generator. For this, the final consumer must grip the grip tab 28 of the seal 27 to detach this from the push-open member 25 or the interface portion 20, thereby exposing the opening 26. As shown in FIG. 2, the container portion 10 is then connected to the interface portion 20 in the region of their connecting regions 19 and 34, respectively. This can be accomplished, for example, by means of a screw connection, in which case the interface portion 20 may have a male thread, and the container portion 11 a female thread. It is, however, also possible to reverse this design. A snap-on connection or a bayonet lock is conceivable just as well. In FIG. 2, the interface portion 20 is not fully screwed into the container portion 10, such that the push-open member 25 in the form of the hollow mandrel is disposed just before the predetermined breaking point 26 of the bottom 15. Further screwing of the interface portion 20 onto the container portion 10 causes further relative motion along the arrow R, with the result that the push-open member 25 is pushed open similarly as described in DE 10 2007 056 462 A1 with respect to the bottom 31, and the bottom 15 is swung aside. This enables, for example, the carrier solution 12 as a constituent of the substance to flow from the chamber 11 in the container portion 10 into the chamber 23 of the interface portion 20 and to mix there with the powder-form active ingredient 24 as the second constituent of the substance to be atomized.

It is then possible to insert the ampoule thus prepared into an aerosol generator, as is described in DE 10 2007 056 462 A1, where the bottom 31 is pushed open along the predetermined breaking line 32 and the mixed substance in the ampoule flows to the aerosol generator, e.g. a vibratable diaphragm having a plurality of holes, as is equally known from the cited prior art, and is atomized therethrough by vibration. The plurality of, for instance, micron-sized holes (ranging, e.g., from 1 to 6 μm) in the diaphragm to be vibrated can be laser-produced (using, e.g., laser drilling).

Another embodiment is depicted in FIG. 3*a*. This differs from the configuration shown in FIGS. 1 and 2 primarily in that the connection between the container portion 10 and the interface portion 20 is made by the manufacturer. Accordingly, the interface portion 20 does not have a push-open member 25, nor does the container portion 10 have a bottom 15. The substance 40 is received in the chamber 11 and the chamber 23 of the container portion 10 and the interface portion 20. The container portion 10 can be connected to the interface portion 20 in the connecting regions 19 and 34, respectively, by means of any hot working method such as, e.g., welding and bonding methods, and also by the aforementioned screw, lock-on or bayonet connections.

A connection made by the manufacturer between the container portion 10 and the interface portion 20 can be seen from FIG. 3*b*, which in this configuration is closer to the embodiment shown in FIGS. 1 and 2. Since the interface portion 20 and the container portion 10 have already been connected by the manufacturer, it is conceivable to protect the connecting regions 19 and 34, which are capable of moving relative to each other, by a hygiene ring 60 to prevent external contamination from being introduced into the interface region and hence into the substance.

Otherwise these embodiments do not differ substantially from those shown in FIGS. 1 and 2.

Another configuration is depicted in FIGS. 4 and 5. The ampoule in FIG. 4 is also composed of a container portion 10 and an interface portion 20. In this arrangement, the design of the interface portion 20 is substantially identical to that of the interface portion 20 of FIG. 1, and identical or comparable elements will not be described again at this point. Instead, reference is made to that stated with regard to FIG. 1. Unlike in the configuration of FIG. 1, the interface portion 20 does not, however, comprise a cutting edge 25, nor is it closed by a seal 27. Rather, the cavity 23 is substantially freely accessible via the opening 26 and no constituent of the substance 40 to be atomized is received in the interface portion 20. In addition, the inner diameter of the cylindrical outline 29 of the interface portion 20 facing the container portion 10 is larger in the connecting region 34 than the outer diameter of the cylindrical wall 18 in the connecting region 18 of the container portion 10.

Here as well, the container portion 10 is substantially cylindrical. It substantially has rotational symmetry about its longitudinal axis L. Unlike in the configuration in FIG. 1, however, two chambers 11 are formed in the container portion 10, which each contain a constituent of a substance to be atomized in an aerosol generator (not shown). Also, unlike in the configuration of FIG. 1, the opposite side of the container portion 10 to the front wall 13, which comprises respective openings 41 to the chambers 11, is closed by a seal 27, instead of the bottom 15 with the predetermined breaking point 16. The seal 27 comprises a grip tab 28 for removing the seal 27 from the openings 41 and exposing the chambers 11. The chambers 11 are defined by the seal 27 as well as by the cylinder walls 14, the front wall 13 and a partition 42.

Prior to using the ampoule, the seal 27 must be removed by gripping the grip tab 28 and pulling the seal 27 off of the openings 41. The interface portion 20 is then connected to the container portion 10 via the connecting regions 19 and 34, respectively. Just as in the embodiment of FIGS. 1 and 2, this can be done by using a screw connection. However, those connections are preferred which rule out the possibility of detaching the container portion 10 from the interface portion 20 after they have been connected and thus after use of the ampoule, in order to avoid any further use of the components which is undesired in clinical practice. The connected condition is shown in FIG. 5*a*. As an alternative to this connected condition, it is also conceivable, as shown in FIG. 5*b*, to close the opening 26 of the interface portion 20—after the chamber 23 of the interface portion 20 has been filled from the chambers 11 of the container portion 10—by a lid 100 which, once applied, can preferably not be detached. This can be accomplished, for example, in that the connecting region 134 of the interface portion 20 comprises one or more protrusions 134 (or recesses) which engage with one or more locking hooks 101 of the lid 100 while this is closed. This lock-on connection can be designed to be permanent such that, once applied, the lid 100 can no longer be detached. As an alternative, the locking hooks could also be attached to the interface portion, and the protrusions or recesses to the lid. During use, the seal 27 is first removed from the container 10, as explained previously, and the substances from the chambers 11 are introduced into the chamber 23 and brought together there—if necessary by connecting the container portion 10 to the interface portion 20. The container portion 10 is then detached again from the interface portion 20, if appropriate, and the lid 100 is locked in place on the interface portion 20.

The constituents of the substance contained in the chambers 11 can then mix or combine in the cavity or chamber 23 of the interface portion 20 to form the substance 40, for example before the ampoule is inserted into an aerosol generator to atomize the substance, as is described in DE 10 2007 056 462 A1.

Otherwise this embodiment does not differ substantially from the configuration described with reference to FIGS. 1 and 2.

Another configuration is shown in FIG. 6; here as well, the container portion 10 and the interface portion 20 are connected by the manufacturer, similarly as explained with reference to FIG. 3. The configuration of container portion 10 and interface portion 20 is substantially identical to the illustrations in FIGS. 4 and 5, and therefore reference is made to the corresponding statements in order to avoid repetition.

Unlike in the previous embodiments, the container portion 10 and the interface portion 20 in this configuration are connected so that these elements are rotatable relative to each other, as is illustrated by the arrow in the cross-sectional views of FIGS. 6*a* and *b*.

The chambers 11 are closed in the region of their openings 41 by a bottom 43 which in the illustrated configuration has two openings 44.

The chamber 23 of the interface portion 20 is also closed by a cover plate 45 on the side of the opening 26 facing away from the bottom 31. The cover plate also has two openings 46.

Prior to use of the ampoule, the container portion 10 and the interface portion 20 are rotated relative to each other, as is indicated by the arrow at the bottom of FIG. 6*a*. As a result, the openings 44 of the bottom 43 and the openings 46 of the cover plate 45 can be brought into congruence, as is shown in FIG. 6*b*. This makes it possible to establish a fluid communication between each of the chambers 11 and the chamber 23 via the openings 44 and 46. It is thus conceivable to bring together, in the chamber 23, constituents of the substance from the chambers 11. It is also conceivable to additionally provide a constituent of the substance in the chamber 23, meaning that three different constituents can be brought together. It is also possible by arranging the openings in the cover plate 45 or bottom 43 to mix the individual constituents in a specific sequence, and/or to define a rate of mixing via the cross-section of the openings. Also, it is, of course, possible to provide three, four or more chambers in a container portion 10 rather than only two chambers, or to respectively connect several container portions 10 to at least one chamber having just one interface portion 20.

This is, in turn, followed by insertion of the ampoule into an aerosol generator, as has already been described above with respect to DE 10 2007 056 462 A1.

Another configuration is explained in FIG. 7. Similarly to FIG. 6, the container portion 10 and the interface portion 20 also rotate relative to each other in the embodiment shown in FIG. 7, to bring together prior to use—in this case in the chambers 11 and 23—constituents of the substance. At the same time, however, this embodiment also involves translational motion. To this end, the connecting portions 19 and 34 may, for example, be designed as screw connections. If the connection is made by the manufacturer, the screw connection is preferably designed to prevent complete separation of the container portion 10 from the interface portion 20, or additional means are provided for this purpose. However, it is also conceivable for the connection to be made for the first time by the user. In that case, a locking hook supposed to prevent any subsequent separation could have to be overcome when screwing the interface portion 20 into the container portion 10.

Unlike in the previous embodiments, the opposite side of the interface portion 20 to the bottom 31 is closed by a front wall 50, and an opening 51 is provided in the cylindrical side wall 29. In the initial state shown in FIG. 7*a*, this opening 51 is covered and thus closed by the cylindrical portion 14 of the wall of the container portion 10.

Prior to use, the interface portion 20 rotates relative to the container portion 10, thus undergoing translational motion into the chamber 11 of the interface portion 10. As depicted in FIG. 7*b*, this places the opening 51 in fluid communication with the chamber 11 via a bypass or a sub-chamber 52, with the result that constituents can be brought together in the chambers 11 and 23 where appropriate, or a substance contained in the chamber 11 flows into an empty chamber 23 before the connection with the aerosol generator is made. As illustrated in FIG. 7*c*, it is conceivable for the opening 51 to be reclosed by further rotation and associated translational motion after the chamber 23 has been filled. This would make it possible to receive several doses in a container portion 10 and to ensure refilling via the opening 51 and the sub-chamber 52 by screwing out the interface portion 20. It is, however, conceivable just as well for the fluid communication of the chambers 11 and 23 via the opening 51 and the sub-channel 52 to be also upheld in the fully screwed-in condition.

Finally, another configuration of the invention is illustrated in FIGS. 8*a* and *b*. Here, the interface portion 20 substantially corresponds to the interface portion 20 in FIGS. 1 and 2, though the seal 27 has been dispensed with and the chamber 23 does not contain substance 24.

The essential difference lies in the fact that use is made of a bag 55, shown in part, which contains the chamber 11 and which is connected to a plastic intermediate piece 56, rather than of the cylindrical container portion 10 made of plastic which is described in the previous embodiments. This intermediate piece 56 has a cylindrical connecting region 19 with a cylinder wall 18, which can be connected to the bag 15 using methods that are known per se. This can be accomplished, for example, by hot-embossing or sealing methods using the circumferential flange 57. As described above, this connecting region 19 cooperates with the connecting region 34 in connecting the container portion 10 to the interface portion 20.

During the connecting process, the bottom 15 is sliced open by the cutting edge along the predetermined breaking point 16, and fluid communication is established between the chamber 23 and the chamber 11 (not visible in the bag 55 in FIG. 8) prior to insertion of the ampoule thus formed into an aerosol generator, as described previously. As illustrated in FIG. 8b, it is alternatively also conceivable to dispense with the bottom 15, in which case the bag 55 is closed all around. To establish the fluid communication, a portion of the bag 55 is punched out by the cutting edge 25 as the connection is being made via the connecting portions 19 and 34, thus establishing the fluid communication between the chamber 11 in the bag 55 and the chamber 23.

It will be appreciated that the present invention is not limited to the foregoing and that various modifications and variations can be made. In addition, the present invention is not limited to the use of a specific substance or of specific constituents thereof.

The invention claimed is:

1. An ampoule for insertion into an aerosol generator, to atomize a substance contained in the ampoule, comprising:
   a container portion which forms a chamber for receiving at least one constituent of the substance; and
   an interface portion which is adapted to fix the ampoule in a receiving portion of the aerosol generator and which has, in a direction in which the ampoule is to be inserted into the aerosol generator, a push-open bottom, wherein
   the container portion and the interface portion are formed by separate parts prior to using the ampoule and the interface portion is closable at the time of use,
   the container portion and the interface portion respectively have a connecting region via which the container portion and the interface portion are connectable to each other, by means of which the interface portion is closable, and
   the interface portion is configured to be closed only once with the container portion, in that the connecting region of the interface portion is configured to prevent the container portion from being detached from the interface portion without being destroyed.

2. The ampoule according to claim 1, wherein the container portion also has, in the direction in which the ampoule is to be inserted into the aerosol generator, a push-open bottom, and the interface portion has, on the opposite side to its bottom, a push-open member for opening the bottom of the container portion.

3. The ampoule according to claim 2, wherein the push-open member is adapted to push the bottom of the container portion open as the container portion and the interface portion are being connected.

4. The ampoule according to claim 2, wherein the container portion and the interface portion, after being connected, are displaceable relative to each other in the direction in which the ampoule is to be inserted into the aerosol generator, and wherein the push-open member is adapted to push the bottom of the container portion open, after the container portion has been connected to the interface portion, by the relative motion between the container portion and the interface portion.

5. The ampoule according to claim 2, wherein the interface portion forms a further chamber and has an opening in the region of the push-open member, to connect the chamber of the container portion to the chamber of the interface portion after the bottom of the container portion has been opened.

6. The ampoule according to claim 5, wherein the opening of the interface portion is closed by a seal, the chamber of the interface portion contains a further constituent of the substance, and the constituents of the substance in the chamber of the container portion and the chamber of the interface portion can be mixed after the seal and the bottom of the container portion have been opened.

7. The ampoule according to claim 1, wherein the container portion and the interface portion are each integrally formed.

8. The ampoule according to claim 1, wherein the bottom of the interface portion and/or the bottom of the container portion lie in a plane perpendicular to the direction in which the ampoule is to be inserted into the aerosol generator.

9. The ampoule according to claim 1, wherein the interface portion and/or the container portion have a circumferential collar which extends a wall of the interface portion or container portion beyond its bottom in the direction in which the ampoule is to be inserted into the aerosol generator.

10. The ampoule according to claim 1, wherein the interface portion has a circumferential, outwardly open groove in a wall, to fix the ampoule in a receiving portion of the aerosol generator.

11. The ampoule according to claim 1, wherein the interface portion and/or the container portion are made, in full or in part, of a soft or hard plastic material by using blow-fill-seal or injection moulding technology, and/or of glass.

12. The ampoule according to claim 1, wherein the container portion and/or the interface portion are disposables that cannot be reused after use.

13. The ampoule according to claim 1, wherein the container portion has two or more chambers.

14. An interface portion for an ampoule for insertion into an aerosol generator comprising:
   a connecting region for connection to a container portion, wherein the interface portion is configured to be closed only once at the time of use with the container portion, in that the connecting region is configured to prevent the container portion from being detached from the interface portion without being destroyed, and wherein the interface portion is adapted to fix the ampoule in a receiving portion of the aerosol generator and has, in a direction in which the ampoule is to be inserted into the aerosol generator, a push-open bottom.

15. The interface portion according to claim 14, wherein the connecting region includes a channel that is adapted to be opened.

16. The interface portion according to claim 14, which is adapted to be connected or combined with a container portion having two or more chambers to form the ampoule.

17. The interface portion according to claim 14, which is adapted for use in a ventilation circuit of a ventilator as a disposable for supplying one or more drug substances to an aerosol generator for aerosol generation.

18. The interface portion according to claim 14, wherein the connecting portion is adapted for connection to an aerosol generator, wherein the aerosol generator is a membrane nebulizer.

* * * * *